United States Patent [19]

Lee

[11] Patent Number: 4,624,848

[45] Date of Patent: Nov. 25, 1986

[54] ACTIVE AGENT CONTAINING HYDROGEL DEVICES WHEREIN THE ACTIVE AGENT CONCENTRATION PROFILE CONTAINS A SIGMOIDAL CONCENTRATION GRADIENT FOR IMPROVED CONSTANT RELEASE, THEIR MANUFACTURE AND USE

[75] Inventor: Ping I. Lee, Berwyn, Pa.

[73] Assignee: Ciba-Geigy Corporation, Ardsley, N.Y.

[21] Appl. No.: 608,756

[22] Filed: May 10, 1984

[51] Int. Cl.[4] .................... A61K 9/26; A61K 31/74
[52] U.S. Cl. ................................ 424/22; 424/19; 424/81
[58] Field of Search .................... 424/12–22, 424/81

[56] References Cited

U.S. PATENT DOCUMENTS

| | | | |
|---|---|---|---|
| 3,390,050 | 6/1968 | Speiser | 424/81 |
| 3,551,556 | 12/1970 | Kliment et al. | 424/81 |
| 3,576,760 | 4/1971 | Gould et al. | 424/81 |
| 3,577,512 | 5/1971 | Shepherd et al. | 424/81 |
| 3,660,071 | 5/1972 | Gould et al. | 424/81 |
| 3,660,563 | 5/1972 | Gould et al. | 424/81 |
| 3,775,537 | 11/1973 | Lehmann et al. | 424/81 |
| 3,959,237 | 5/1976 | Blank | 424/81 |
| 3,997,482 | 12/1976 | Turkova et al. | 424/81 |
| 4,007,258 | 2/1977 | Cohen et al. | 424/81 |
| 4,056,496 | 11/1977 | Mancini et al. | 424/81 |
| 4,070,348 | 1/1978 | Kraemer et al. | 424/81 |
| 4,164,560 | 8/1979 | Folkmon et al. | 424/19 |
| 4,177,056 | 12/1979 | Mueller et al. | 424/81 |
| 4,178,361 | 12/1979 | Cohen et al. | 424/81 |
| 4,248,855 | 2/1981 | Blank et al. | 424/81 |
| 4,267,295 | 5/1981 | Gallop et al. | 424/81 |
| 4,304,591 | 12/1981 | Mueller et al. | 424/81 |
| 4,357,312 | 11/1982 | Hsieh et al. | 424/15 |
| 4,411,754 | 10/1983 | Kaetsu et al. | 424/81 |

FOREIGN PATENT DOCUMENTS 0111144 6/1984 European Pat. Off.

*Primary Examiner*—Shep K. Rose
*Attorney, Agent, or Firm*—Michael W. Glynn

[57] ABSTRACT

An active agent containing controlled release diffusion device comprising a swellable hydrogel matrix in the non-swollen state, interpenetrated with an active agent solute having a stable concentration distribution increasing in a gradient normal to the surface of the device and between the surface and the core thereof, said gradient being in the form of a substantially continuous, inflection point containing, sigmoidal curve, such that the device, when placed in an aqueous hydrogel swelling environment, releases said active agent in a controlled continuous manner by diffusion for a predetermined period of time, a method of preparing such a device, and the use thereof to release an active agent into the intended environment of use.

12 Claims, 9 Drawing Figures

FIG. 1a

FIG. 1b

Figure 2A:
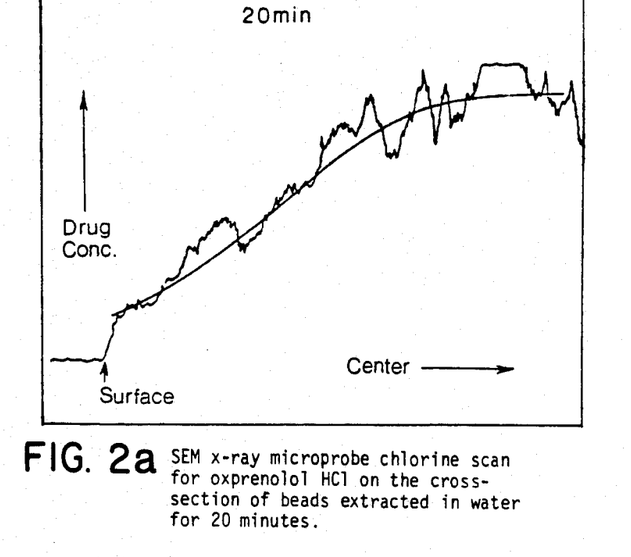

FIG. 2a SEM x-ray microprobe chlorine scan for oxprenolol HCl on the cross-section of beads extracted in water for 20 minutes.

Figure 2B:
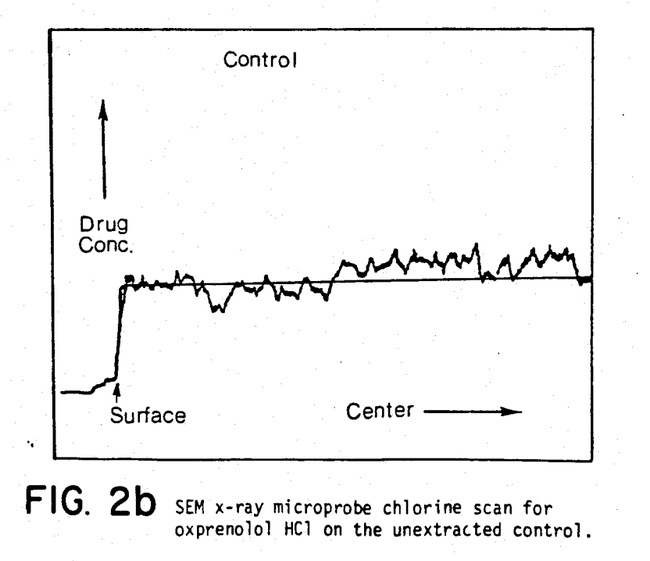

FIG. 2b SEM x-ray microprobe chlorine scan for oxprenolol HCl on the unextracted control.

Figure 3A:
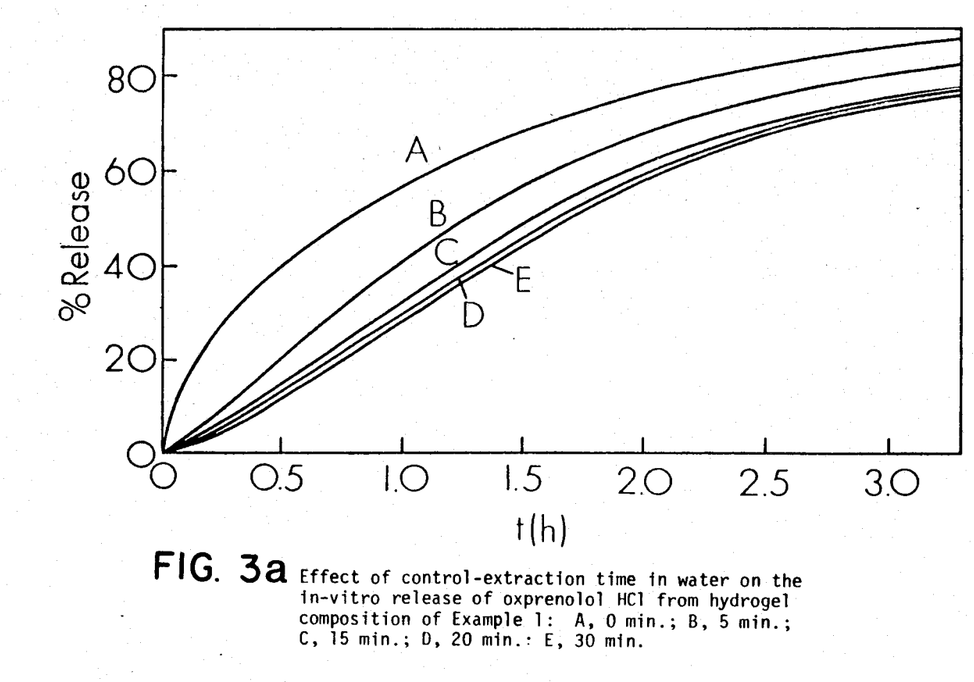

FIG. 3a Effect of control-extraction time in water on the in-vitro release of oxprenolol HCl from hydrogel composition of Example 1: A, 0 min.; B, 5 min.; C, 15 min.; D, 20 min.; E, 30 min.

Figure 3B:
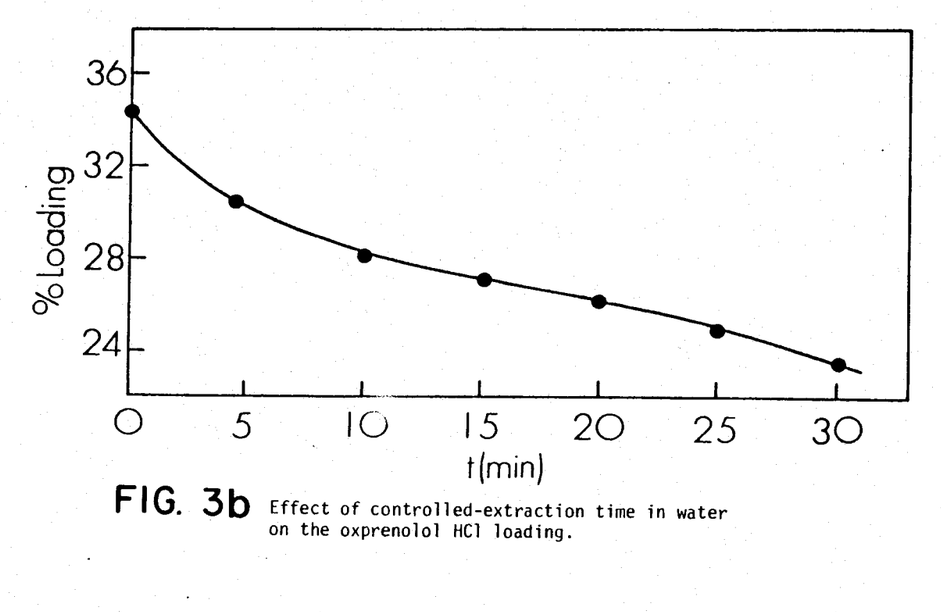

FIG. 3b Effect of controlled-extraction time in water on the oxprenolol HCl loading.

Figure 4A:
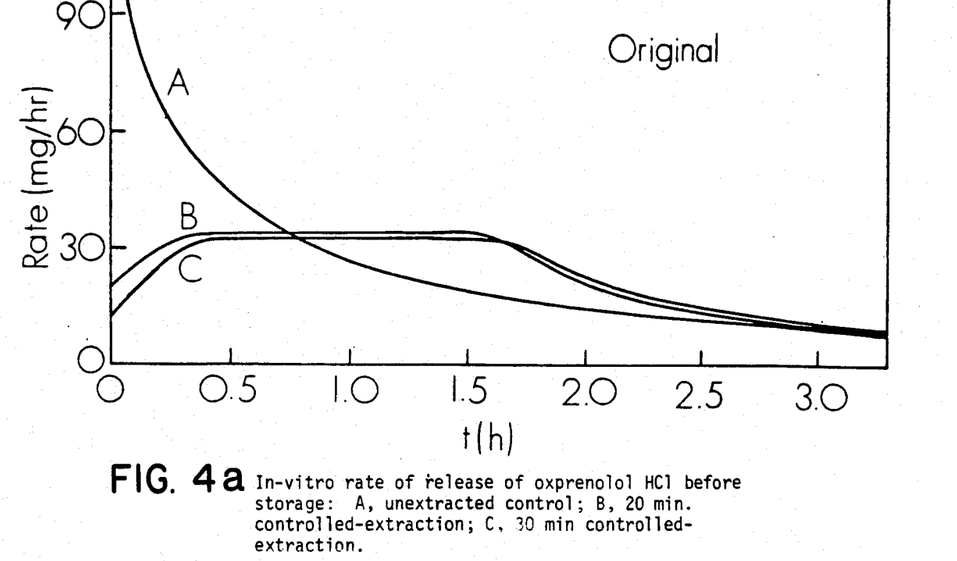

FIG. 4a In-vitro rate of release of oxprenolol HCl before storage: A, unextracted control; B, 20 min. controlled-extraction; C, 30 min controlled-extraction.

Figure 4B:
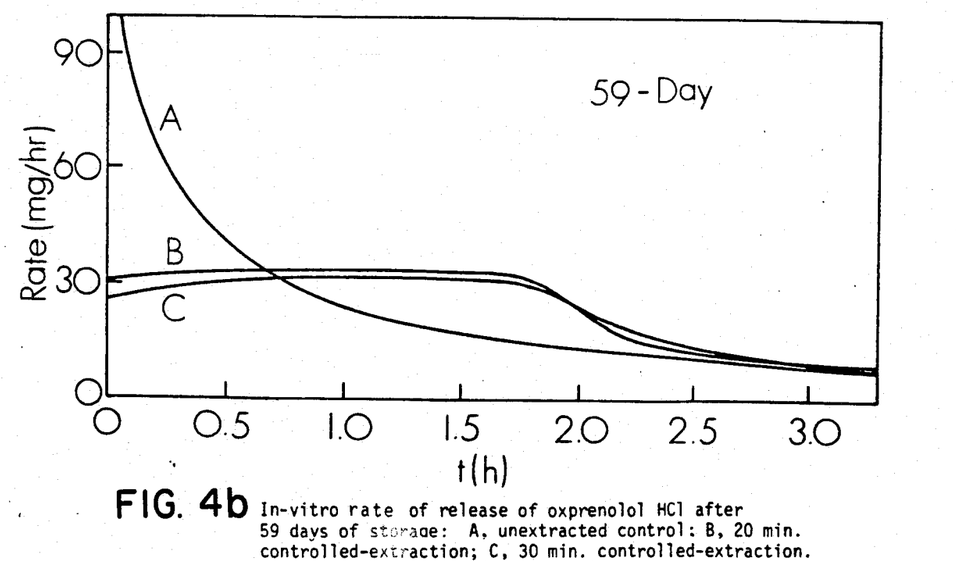

FIG. 4b In-vitro rate of release of oxprenolol HCl after 59 days of storage: A, unextracted control; B, 20 min. controlled-extraction; C, 30 min. controlled-extraction.

Figure 5:
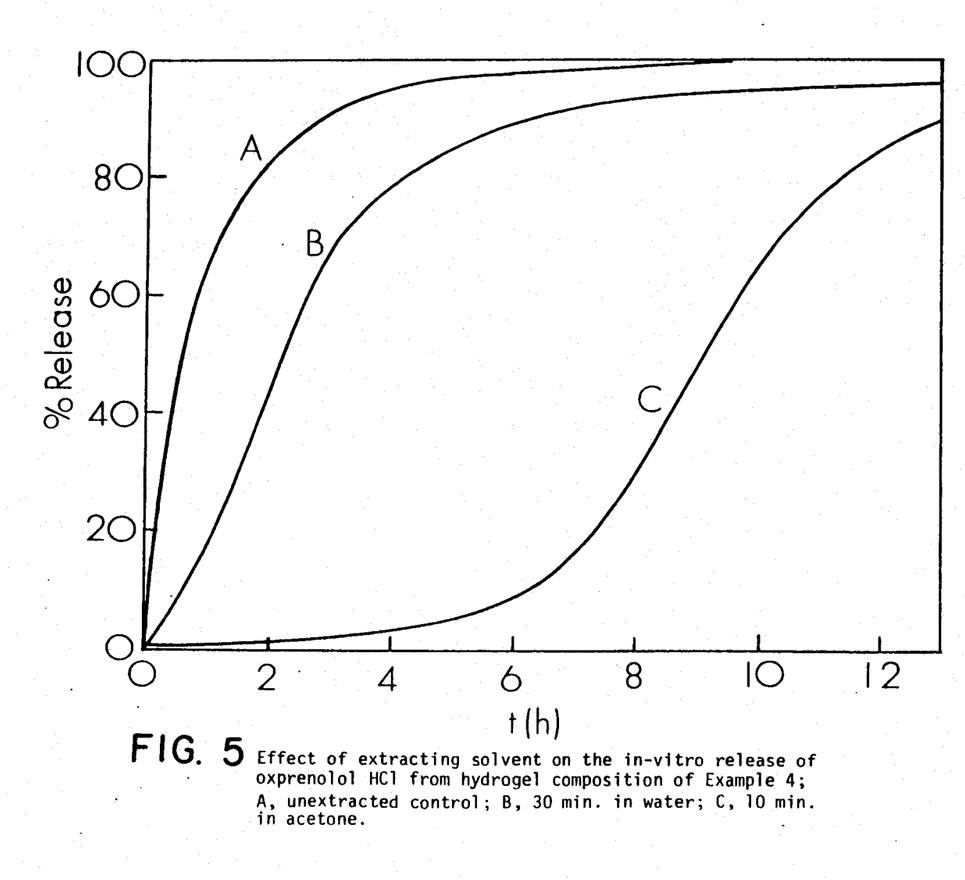

FIG. 5 Effect of extracting solvent on the in-vitro release of oxprenolol HCl from hydrogel composition of Example 4; A, unextracted control; B, 30 min. in water; C, 10 min. in acetone.

ACTIVE AGENT CONTAINING HYDROGEL DEVICES WHEREIN THE ACTIVE AGENT CONCENTRATION PROFILE CONTAINS A SIGMOIDAL CONCENTRATION GRADIENT FOR IMPROVED CONSTANT RELEASE, THEIR MANUFACTURE AND USE

BACKGROUND OF THE INVENTION

The present invention relates to a hydrogel device containing an active agent which is released by diffusion to an aqueous medium upon contact therewith at a controlled rate for a predetermined period of time, a method for preparing such a device and a method of use of such a device to release the active agent into the aqueous medium.

Various devices are known in the art for the sustained release of an active agent. For example, monolithic devices for sustained release of agent, wherein the agent is dispersed uniformly in a non-swellable homogeneous and imperforate polymer matrix where the agent dissolves in and permeates through the polymer itself are known. Microporous devices, in which the pores contain an active agent permeable liquid or gel medium such that the active agent preferentially dissolves in and permeates through the medium in the pores, are also known, as well as osmotic bursting devices wherein water is imbibed osmotically into active agent depots in a water permeable-active agent impermeable polymer matrix to rupture the depots serially. Characteristically, such devices release the active agent at a high initial rate which then drops off in the manner of a first order equation.

The release of an active agent from a uniformly dispersed agent in a non-swellable homogeneous and imperforate plasticized polymer matrix by active agent permeation can be classified as a classical Fickian release, since the release pattern generally follows Fick's law of diffusion;

$$M_t = Kt^{\frac{1}{2}}$$

where $M_t$ is the amount active agent released, K is a constant and t is time.

U.S. Pat. No. 3,923,939 describes the removal of a portion of active agent from the surface of the aforementioned prior art diffusion and osmotic bursting devices by washing to form a depleted layer of polymer matrix. However, the devices do not include hydrogels, and moreover still generally exhibit a Fickian release, albiet with a lower initial release as evidenced by the release profile of the diffusion type devices of Example 1A with those of 1B in FIGS. 3 and 4 of that patent. The only anomolous release pattern described and exemplified is that of an osmotic bursting device in which the bursting device was washed for 24 hours such that the initial release rate was decreased by 90% as described in Example 3B and FIG. 10 of U.S. Pat. No. 3,923,939.

One drawback of the drug diffusion devices of the type exemplified in Example 1B of the aforementioned patent is that after treatment of the surface, the drug will diffuse at a rate corresponding to the drug diffusion rate in the device matrix until the drug is again uniformly distributed throughout the diffusion device. As a result, such a drug soluble rubbery polymer system exhibits numerous drawbacks.

Active agent releasing devices containing a swellable hydrogel matrix are also known in the art. In such devices, the active agent is uniformly distributed in the non-swollen, or glassy, hydrogel polymer. Upon contact with an aqueous environment, the dry hydrogel swells as water penetrates the glassy matrix. The boundary between the glassy phase and the swollen, or rubbery, phase of the hydrogel is known as the solvent front. As the aqueous solvent front moves inward from the surface to the center of the hydrogel device, the active agent in the rubbery swollen phase of the hydrogel dissolves and diffuses through the swollen phase into the external aqueous environment. The active agent is substantially incapable of diffusion to any significant extent in the glassy non-swollen phase of the hydrogel. The rate of active agent transport into an aqueous environment is dependent upon a number of factors including the rate of penetration of the aqueous solvent front, the shape of the device, the diffusivity of the active agent in the swollen phase, the amount of active agent loading in the hydrogel matrix, the distance between the solvent front and the surface of thw device, the rate of decrease of the surface area of the glassy phase during solvent penetration and the like. See, for example, Ping I. Lee, *Polymer Comunications,* Vol. 24, p. 45–47 (1983).

Characteristically, the release rate for such hydrogel devices, containing uniformly distributed active agent, generally conforms to the following equation $$M_t = Kt^a$$

where $M_t$ is the amount of active agent released, K is a constant, t is time and a is between about 0.8 and 0.5. As a result, such systems do not provide for a substantially zero-order release, since the rate of release continuously drops off from a high initial release rate.

SUMMARY AND OBJECTS OF THE INVENTION

It is an object of the instant invention to provide an improved device comprising an aqueous swellable hydrogel matrix containing an active agent solute such that the release rate of the active agent by diffusion from the device is substantially zero order for an extended period of time.

It is a further object of the instant invention to provide a method of delivering an active agent into an aqueous environment at a substantially constant rate for an extended period of time by the use of such an improved device.

These and other objects of the invention can be obtained by providing a stable active agent solute non-uniform profile in the hydrogel matrix, such that the concentration of active ingredient increases in a gradient normal to and between the surface of the device to the core of the device, wherein the concentration gradient is in the form of a substantially continuous, i.e. smooth, inflection point containing sigmoidal curve.

The substantially continuous inflection point containing sigmoidal concentration distribution of the active agent from the surface to the core of the device thus increases in an increasing slope to an inflection point located between the surface and the core, and then increases in a decreasing slope from the inflection point to the core.

Such a sigmoidal curve containing profile cannot be obtained by merely washing an active agent loaded hydrogel device while in the fully swollen state, such as immediately after wet loading the active agent into the hydrogel and prior to drying the loaded device. In such a rubbery, fully swollen device, the removal of active agent, for example by washing the surface thereof, generally results in a concentration profile which increases from the surface to the core in a decreasing slope. Such an overall profile can be characterized as a "parabolic" concentration profile, as contrasted with a sigmoidal or "bell-shaped" concentration profile obtained according to the instant invention. Moreover, the parabolic concentration profile characteristally results in a time dependent release rate with a diminished initial rate.

It has now been found that a sigmoidal curve containing profile can be obtained by washing the surface of an active agent solute uniformly loaded hydrogel device which is initially in the non-swollen, or glassy, state, with a volatile swelling solvent for a time sufficient for the solvent to penetrate the outer surface of the device such that the device has an outer swollen, or rubbery, phase and an inner non-swollen, or glassy, phase or core, to thereby remove a portion of the active agent from the rubbery phase, and then rapidly removing the volatile solvent from the hydrogel device at a rate sufficient to immobilize the active agent in a stable concentration distribution in an increasing fashion from the surface to the core of the device whereby the gradient is in the form of a continuous inflection point containing sigmoidal concentration curve.

As the solvent is removed, the swollen phase reverts to the non-swollen, glassy state. Accordingly, the desired concentration profile is obtained as a storage stable product, since the diffusivity of an active agent solute is characteristically at least several orders of magnitude less in a glassy hydrogel than in a swollen, or rubbery, hydrogel.

The process conditions and the nature of the swelling solvent are selected to provide the desired distribution, such that when the dried glassy hydrogel is subsequently placed in an aqueous hydrogel swelling environment of use, the improved device releases the active agent in a controlled substantially constant rate for a predetermined period of time. Such process parameters of the active agent extraction include time and temperature. For any given temperature, the amount of penetration of the swelling solvent is time dependent. Similarly, the rate of diffusion of the active agent in the swollen portion of the hydrogel increases with increasing temperature, as does the rate of penetration of the solvent front. Thus, in some instances, accelerated extraction of a portion of the active agent by the use of elevated temperature conditions is desirable. Also, agitation of the swelling solvent, and/or removal of active agent containing swelling solvent during the extraction of the active agent from the initially uniformly loaded hydrogel device, such as by washing, may be advantageously employed. Generally the temperature of extraction may vary widely, for example, between about $-20°$ to about $120°$ C., depending on the freezing and boiling point of the volatile swelling solvent chosen. If desired, superatmospheric presence conditions may be employed during the extraction step. Desirably, the temperature of the extraction step is chosen so as to be below the glass transition temperature of the loaded hydrogel. When the temperature of the extraction step is greater than the glass transition temperature of the loaded hydrogel, the diffusivity of the active agent in the unswollen portion of the device increases greatly. Accordingly, it is preferred that the extraction temperature be between about $-20°$ C. up to about $120°$ C. but not in excess of the glass transition temperature of the loaded hydrogel. The glass transition temperature of loaded hydrogels is dependent in part on the nature of the hydrogel chosen, but is generally preferred between about $45°$ to about $120°$ C. or even higher. It is more preferred to use hydrogels having a loaded glass transition temperature of above $50°$ C. and to conduct the extraction step at a temperature between about $10°$ C. to $50°$ C.

It is important that the controlled extraction swells only the exterior of the device such that there is an unswollen core remaining in order to obtain the desired sigmoidal concentration profile. Generally, between about 15 to 98 volume percent of the device is at least partially swollen during the profile modification process, preferably about 20 to 90 volume percent is at least partially swollen. There is accordingly removed from the loaded hydrogel, about 7 to 80 weight percent, preferably between 15 to 75 weight percent, active agent, based upon the amount of active agent originally present.

It is a critical aspect of the instant process that the sigmoidal concentration profile generated during the aforementioned extraction step be substantially retained during the solvent removal step in order to immobilize the active agent in this desired profile. This can be accomplished by rapidly removing the swelling solvent from the swollen portion of the hydrogel matrix. By rapid removal in this context is meant that the rate of removal of the swelling solvent is substantially greater than the rate of diffusion of the active agent in the swollen portion of the hydrogel.

Advantageously, the desired rapid removal of the volatile swelling solvent can be effected by reducing the pressure of the system under isothermal or adiabatic conditions to remove the solvent by evaporation. The degree to which the pressure is reduced will depend on the nature of the volatile swelling solvent and the temperature. Since it is desired to quickly remove the solvent so as to minimize active agent diffusion, a high vacuum is desirable. Advantageously, the pressure is reduced to below 70 mm Hg, preferably lower than 10 mm Hg, most preferably below 0.1 mm Hg. Highly desirable is a reduction of pressure to $1 \times 10^{-3}$ mm Hg and lower. The reduction in pressure may be achieved under substantially adiabatic conditions, under moderate heating conditions or with cooling. Temperatures above the glass transition temperature should ordinarily be avoided, in order to minimize diffusion of the active agent. Moreover, low temperatures combined with low pressure are ordinarily advantageous to insure immobilization of the active agent in the desired sigmoidal concentration profile between the device surface and the core thereof, while rapidly removing the volatile swelling solvent. Adiabatic rapid reduction of pressure characteristically results in a considerable lowering of the temperature of the device, thereby assisting in the immobilization of the desired profile. Conventional freeze drying conditions may be used.

The hydrogels useful in this invention are generally all water swellable, but water insoluble polymers. Such polymers are, for instance, synthesized by free radical copolymerization of a water soluble vinyl monomer with a difunctional crosslinking agent; crosslinked poly-2-hydroxyethyl methacrylate and poly-vinylpyrrolidone are two of the most widely known and used hydrogels, but other water soluble monomers can also be used in the preparation of hydrogels as well as a large variety of comonomers and of crosslinking agents. Especially useful are hydrogels prepared by copolymerization with macromeric crosslinking agents, as described in U.S. Pat. No. 4,192,827. Other useful hydrogel compositions are described in U.S. Pat. Nos. 3,220,960; 3,520,949; and 3,503,942.

Water soluble vinyl monomers useful for the preparation of hydrogels include, but not exclusively, the hydroxyalkyl esters and amides of acrylic and methacrylic acid, such as 2-hydroxyethyl acrylate or methacrylate, 2- and 3 -hydroxypropyl acrylate and methacrylate; 2,3-dihydroxypropyl methacrylate; compounds of structure where R and R' are hydrogen, methyl or ethyl and n is an integer from 2-50. Hydroxyalkyl mono esters and diesters of maleic or fumaric acid, and their ethoxylated derivatives, like di-2-hydroxyethylmaleate and fumarate; and 2- and 3-hydroxypropylbutyl fumarate are similarly useful, as are hydroxy alkyl vinyl ethers, such as 2-hydroxyethyl vinyl ether and 4-hydroxybutyl vinyl ether. Other useful monomers are N-vinyl pyrrolidone and N-vinyl pyrrolidine, 4- and 2-vinyl-pyridine; N,N-dialkylamino alkyl esters and amides of acrylic and methacrylic acid, like N,N-dimethylamino ethyl methacrylate and methacrylamide; N,N-dimethylaminoethyl vinyl ether, N-methylol acrylamide, acrylic acid, methacrylic acid, sodium-styrene and sodium vinyl sulfonate, acrylamide and methacrylamide.

These monomers can be used alone and in combination with each other, and may be copolymerized with suitable hydrophobic vinyl monomers, like styrene, acrylates and methacrylates, vinyl esters and vinyl ethers; maleates, fumarates and vinyl ethers require the presence of comonomers for polymerization to proceed. Also useful is poly-vinyl alcohol in crosslinked or linear state as well as vinyl alcohol copolymers with ethylene, acrylates, vinylesters, and vinylpyrrolidone copolymers with vinylesters.

The crosslinking agent employed in making the hydrogel may be a di- or poly-functional vinyl compound of 200–10000 molecular weight and be present in the polymerizing mixture in amounts ranging from 0.1% (for low MW crosslinkers) to 60% (for high MW crosslinkers).

Other useful hydrogel materials are polyethylene oxide containing polycondensates, such as polyurethanes from diisocyanates and polyethylene oxide diols of 300–10000 MW; polyesters from diacids, diacid chlorides or anhydrides and polyethylene oxide diols of 300–10000 MW; unsaturated polyesters devised from maleic- or fumaric acid and polyethylene oxide diols and copolymerized with styrene or acrylic monomers to a crosslinked polymer; epoxy polymers derived from diepoxides and the 3-amino-propyl ethers of polyethylene oxide diols; polyamides from diacids, diacid chlorides and anhydrides and 3-aminopropyl ethers of polyethylene oxide diols of 300–10000 MW. By those knowledgeable in the art of polycondensation any number of polyethylene oxide polymers can be prepared containing a large variety of co-reactants, having preferably at least 10% by weight of polyethoxy-units which can be classified as hydrogels. Polycondensation hydrogels are described, for instance, in U.S. Pat. No. 3,822,238.

Also useful in this context are hydrogels prepared by free-radical initiated copolymerization of unsaturated polyesters based on maleic anhydride and alkylene diols with water-soluble vinyl monomers, vinyl pyrrolidone, 2-hydroxyethyl methacrylate, or hydroxy alkyl-vinylethers.

The hydrogels may also contain polysiloxane units, as described in U.S. Pat. No. 4,136,250, or contain perfluoro alkyl substituted side chains. Other useful substrates include water swellable polymers derived from natural products, such as cellulose or proteins, for example reconstituted cellulose films, and hydroxy-ethyl cellulose, or gelatin and albumin derived polymers.

In general, the term 'hydrogel' encompasses not only crosslinked water-swellable polymers, but also linear polymers which, like high molecular weight fully hydrolyzed polyvinyl alcohol, dissolve only with difficulty or not at all in the environment of use, forming in effect a linear hydrogel. Even water soluble polymers can be used in the context of this invention as long as they do not dissolve during the application of the process of the present invention.

The most preferred hydrogels for the purpose of carrying out this invention are hydrogel beads as they are obtained by suspension polymerization of hydroxyalkylacrylates or methacrylates, or N-vinyl-pyrrolidone containing mixtures. Such beads and the process for making them are described in U.S. Pat. No. 4,224,427, incorporated herein by reference.

In the context of this invention, a hydrogel is defined as a polymer having an effective degree of swelling in water of at least 5% by weight water.

Drugs used to treat the body, both topical and systemic, can be incorporated as the active agent in the carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug, the desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided, for example, anabolics, e.g. methandrostenolone; analgesics, e.g. acetylsalicylic acid, phenylbutazone or methadone; androgens, e.g. methyltestosterone; antibiotics, e.g. rifampin; antidepressants, e.g. imipramine or maprotiline; antidiabetics; e.g. phenformin; anticonvulsives, e.g. carbamazepine; antihistamines, e.g. tripelennamine; antihypertensives, e.g. hydralazine; antiinfectives, e.g. trimethoprim; antiparasitics, e.g. nifurtimox; antiparkinson agents, e.g. levodopa; antiphlogistics, e.g. naproxen; antitussives, e.g. benzonatate; appetite depressants, e.g. mazindol; bronchodilators, e.g. fenoterol; coronary dilators, e.g. fenalcomine; corticoids, e.g. dexamethasone; cytostatics, e.g. floxuridine; diuretics, e.g. hydrochlorothiazide; hypnotics, e.g. glutethimide; neuroleptics, e.g. reserpine or thioridazine psycho-analeptics, e.g. methylphenidate; tranquilizers, e.g. diazepam; uricosurics, e.g. sulfinpyrazone; vasodilators, e.g. isoproterenol.

In addition to drugs, there can be incorporated in the copolymers of the instant invention fragrances or food flavors, biocides, including bactericides, fungicides, insecticides, nematocides, and herbicides.

Other examples of biologically effective ingredients are listed in U.S. Pat. No. 3,660,563 (columns 3 to 7).

It is important that the active agent be sufficiently soluble in the aqueous environment of use, i.e. a solute for the aqueous environment, so as to diffuse through the swollen hydrogel upon aqueous activation to an extent sufficient so as to achieve the desired effect. Preferably, the active agent is substantially solid in the dry state. This further reduces the amount of diffusion which may occur when desired the active agent profile is obtained in the glassy state and thereby enhances the storage stability of the sigmoidal concentration profile.

The active agent loaded hydrogel starting materials for the instant invention ordinarily possess a uniform active agent concentration and are in the glassy or non-swollen state.

Such starting materials are known or are easily obtained, for example, by immersing the hydrogel in solutions of the active agents in solvents or solvent mixtures which are swelling agents for the hydrogel. Suitable swelling agents include water, lower alkanols, lower alkanones, methylene chloride, dimethylformamide, dimethylsulfoxide, water-lower alkanol mixtures, water-lower alkanone mixtures and the like. to remove the swelling solvent under ambient or reduced pressure.

Volatile swelling solvents useful for removing a portion of the active agent from the glassy or non-swollen loaded hydrogel incude water, lower alkanols of up to 5 carbon atoms, lower alkanones of up to 5 carbon atoms, methylene chloride and miscible mixtures thereof.

While the shape of the hydrogel device is not critical, and may be in the form of rounded cylindrical tablets, corneal lenses, rods, cubes, sheets, tubes, and the like, the hydrogel device is preferably generally spherical in shape, e.g. in the form of a bead. Preferably, such beads may vary in size between about 0.01 mm to about 20 mm in diameter depending upon the desired application.

When the improved device of the instant invention is activated by an aqueous fluid, such as water, body fluids, including gastric fluid, tear fluid, intestinal fluid and the like, rain water, soil moisture and sea water, the water diffuses into the device, swelling the same from the surface inwardly. As the fluid penetrates the device, the active agent diffuses from the swelling and swollen region to the environment. The release rate is thus dependent upon the rate of active agent in the swollen region and the like. By utilizing the instant unique active agent profile, superior constant release rate characteristics can thus be achieved.

When the improved device, containing the active agent in the sigmoidal concentration profile, is actuated by placing the same into the aqueous environment of intended use, the active agent is released from the device in a controlled continuous manner by diffusion.

Preferably, at least 40 weight percent of the active agent released upon such actuation is released at substantially a constant, or zero-order rate. Most preferably, at least 50 weight percent of the active agent released at substantially a zero order rate. The improved devices of the instant invention are especially advantageous in the release of active agents where the effective dose thereof is relatively close to the dose above which side effects may arise. Unlike prior art systems having a release rate which is initially high, for example approaching or exceeding that which undesirable side effects may be manifested, and then drops off to below the optimum effective dose release rate, the instant devices can be designed to release active agent at the optimum release rate while minimizing the risk of overdose at any time. While such release rate characteristics are in theory attainable by covering a loaded hydrogel with a rate controlling membrane, such membranes tend to crack or rupture due to the swelling characteristics of the hydrogel substrate.

In one embodiment of the invention, the improved device is in the form of a hydrogel bead, wherein the core, substantially uniformly loaded with active agent, extends from the center of the device outwardly to comprise about 1% to about 60% of the radius of the bead; the sigmoidal concentration gradient of the active agent extends to cover about 99% to about 30% of the radius, and there may be present a substantially uniform at least partially depleted outer portion constituting 0 to about 10% of the radius of the bead. Within the sigmoidal concentration gradient, the inflection point may be offset up to about 30%, preferably not more than 20%, and most preferably not more than 15% from the center of the gradient in either radial direction. Where there is a substantially uniform at least partially depleted outer portion, there is preferably present no more than 10 weight percent per unit volume of active agent, as compared to the core concentration of active agent.

Figure 1A:
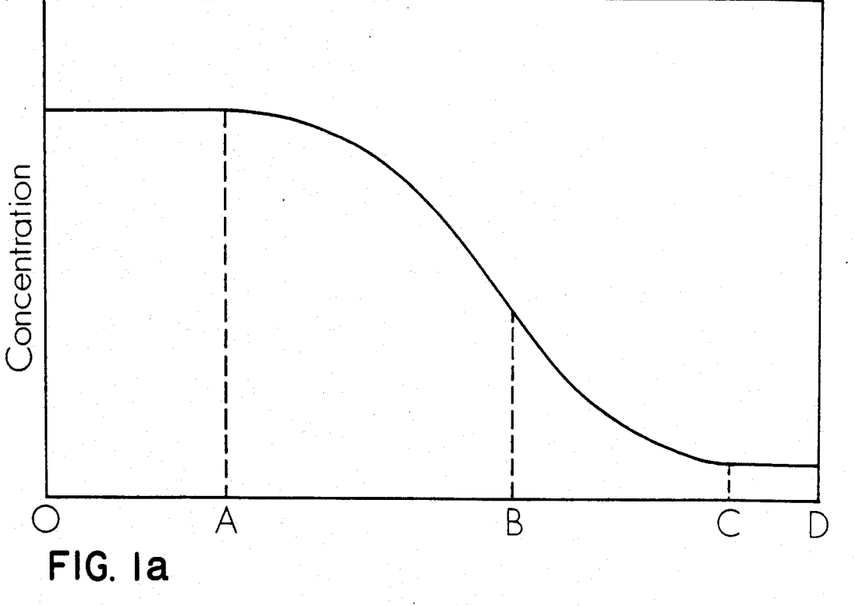
Figure 1B:
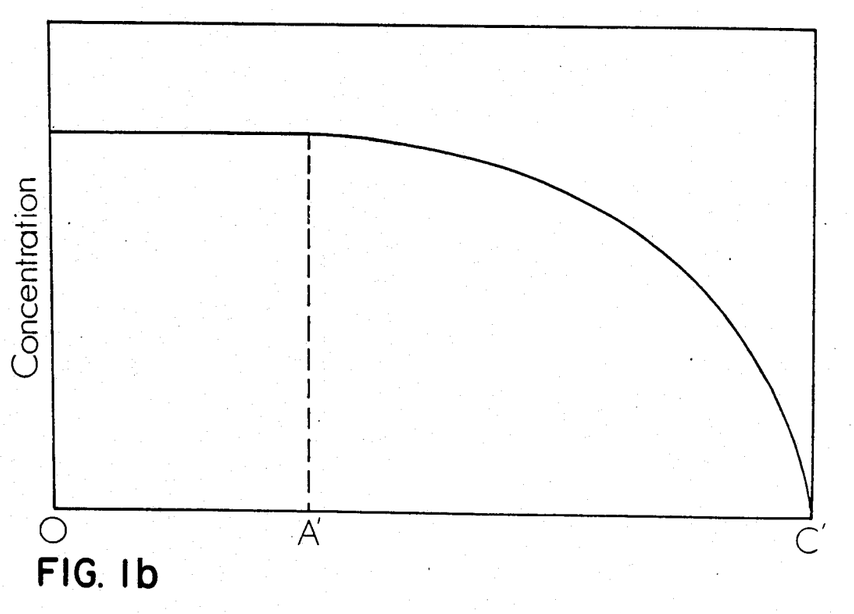

FIG. 1a depicts a representative active agent concentration profile according to the instant invention, where O is the center of the device and D is the surface thereof, segment OA represents the radius of the core, segment AC represents the radial segment containing the sigmoidal concentration gradient, the point B represents the inflection point thereof, and the optionally present segment CD represents the at least partially depleted outer portion of the device. FIG. 1b depicts a representative active agent profile generated by merely washing a uniformly loaded fully swollen hydrogel device, where O is the center of the device, C' is the surface thereof, the segment OA' represents the radius of the core and the segment A'C' represents the parabolic concentration profile.

All compositions in the following examples are expressed in weight percentage unless otherwise noted.

EXAMPLE 1

Hydrogel beads used in this example were prepared by free radical suspension polymerization of a monomer mixture containing 70% of a 2-hydroxyethylmethacrylate (HEMA) and 30% of a polymeric crosslinking agent (PX) derived from poly(tetramethyleneoxide) of average molecular weight 2,000 by end capping with isophoronediisocyanate followed by reaction with excess HEMA as described in U.S. Pat. Nos. 4,177,056 and 4,224,427. After the completion of polymerization, these beads were filtered and extracted in a Soxhlet with ethanol for 24 hours before being dried and fractionated into standard mesh sizes for use in the present invention. Said dry hydrogel beads exhibit a glass transition temperature (Tg) of about 116° C. as determined by differential scanning colorimetry (DSC), an equilibrium water swelling of about 25%, and an equilibrium ethanol swelling of about 49%.

2.5 gm of the said hydrogel beads of −16+18 mesh fraction with an average diameter of 1.1 mm were equilibrated for 24 hours in 12.5 gm of a 50% oxprenolol HCl solution prepared in a mixture of 60% ethanol and 40% water. After filtering and very brief rinsing, the swollen loaded beads were dried at 50° C. under vacuum (∼0.1 mm Hg) to yield a drug-polymer composite system with a uniformly distributed 34.4% oxprenolol HCl loading. Said dry, oxprenolol HCl loaded beads were divided into five portions and subjected to controlled-extraction in an excess volume of water under stirring at 23° C. for periods of 5,15,20 and 30 minutes respectively. One control portion of the dry, loaded beads was not extracted. Immediately after separating the extracting solvent, the controlled-extracted beads were freeze-dried under high degree of vacuum (∼0.025 mm Hg) for about 15 hours. Such a process immobilizes a sigmoidal drug concentration profile with an apparent inflection point within the dry hydrogel matrix in contrast to the uniform drug concentration profile in the untreated control as demonstrated by the experimentally determined SEM X-ray microprobe chlorine scans for oxprenolol HCl across the cross-sections of both the 20-minute extracted and the unextracted control beads (shown in FIGS. 2a and 2b).

The in-vitro releases of oxprenolol HCl from these controlled-extracted beads described above are compared with that of the unextracted control in FIG. 3a. It is evident that an inflection point, corresponding to the inflection point in the drug concentration profile, and a constant-rate release region (up to 60% of the total release) exist in the cumulative release curves of the controlled-extracted beads of the present invention. This is distinctively different from the absence of these release features from the corresponding unextracted control. In addition, FIG. 3a shows that the $t_{50}$'s (time to reach 50% release) are further extended (more than doubled) by the present invention as compared to that of the control and time-lags (obtained by extrapolating the linear release region to the time axis) of up to 0.13 hours are obtained by the present invention as compared to the total absence of a time-lag in the unextracted control. The effect of controlled-extraction time on the oxprenolol HCl loading is shown in FIG. 3b. Only about 10% of the drug loading is removed at an extraction time as long as 30 minutes.

EXAMPLE 2

This example illustrates the storage stability of systems prepared according to the present invention.

Example 1 was repeated except that 7.5 gm of −16+18 mesh beads was used for the initial loading of oxprenolol HCl and only the 20 and 30-minute controlled-extracted beads in addition to the unextracted control were prepared. The amounts of loading solution and extracting solvent used were proportionally increased according to Example 1.

The samples so prepared were divided into portions sufficiently large to provide dose forms equivalent to 100 mg oxprenolol HCl and stored in capped vials under room conditions. The in-vitro release profiles of samples stored for 25 and 59 days are almost identical to that of the sample with no storage time. A comparison of oxprenolol HCl release rates at 0 and 59-day storage from the unextracted control and controlled-extracted beads of the present invention is shown in FIGS. 4a and 4b. The very little change observed in the release profiles is a direct indication that the sigmoidal drug concentration profile generated by the present invention can be substantially preserved indefinitely. The specific feature of the prolonged constant-rate release from the controlled-extracted sample in contrast to the exponential decay of release rate in the unextracted control is also evident from FIGS. 4a and 4b.

EXAMPLE 3

This example illustrates the importance of applying the controlled-extraction step of the present invention to a dry, glassy, drug loaded hydrogel matrix in order to generate the desired inflection point, time lag, and constant-rate release region in the cummulate release profile.

The hydrogel composition and oxprenolol HCl loading procedure of Example 1 were utilized. Immediately after equilibrating the hydrogel beads in the drug solution, a portion of the swollen, loaded beads were subjected to the controlled-extraction step in water for 30 minutes and subsequently freeze-dried under high degree of vacuum. Another portion of the swollen, loaded beads were dried before subjected to the controlled-extraction in water for 30 minutes and the subsequent freeze-drying step as described in Example 1. The in-vitro oxprenolol HCl release from the latter showed a characteristic inflection point, time lag, and a substantial constant-rate region in the cumulative release curve, however the former showed only a slight reduction in the initial release rate as compared to the control, and the inflection point, time lag and constant-rate region were distinctively absent.

EXAMPLE 4

This example illustrates the need of a freeze-drying process instead of drying at a temperature near or above the glass transition temperature of the swollen drug-polymer composite in order to ensure the occurrance of the desired inflection point, time lag, and constant-rate region in the cumulative release profile.

Hydrogel beads with composition similar to that of Example 1 except that 65% instead of 70% HEMA and 35% instead of 30% PX were used in the suspension polymerization. Said hydrogel beads exhibit a glass transition temperature of about 115° C., an equilibrium water swelling of about 20%, and an equilibrium ethanol swelling of about 45%. The hydrogel beads so prepaed were subjected to the same purification, oxprenolol HCl loading and drying steps as in Example 1. The dry loaded beads were controlled-extracted in water for 30 minutes. One portion of the extracted beads was immediately freeze-dried as in Example 1, whereas another portion was dried in a vacuum over at an elevated temperature of 50° C. The in-vitro oxprenolol HCl release from the freeze-dried portion showed a characteristic inflection point, time, lag, and a substantial constant-rate region in the cumulative release curve, however the portion dried at 50° C. showed only a slight reduction in the initial release rate as compared to the control, and the inflection point, time lag, and constant-rate region were distinctively absent.

EXAMPLE 5

This example illustrates the effect of different solvent used in the controlled-extraction step on the oxprenolol HCl release from another glassy hydrogel composition.

Hydrogel beads used in this example were prepared by free radical suspension polymerization of a monomer mixture containing 21% HEMA, 12% PX (defined in Example 1), 12% N-vinylpyrrolidone (NVP), 27.5% ethyl hexylactylate (EHA), and 27.5% methyl methacrylate (MMA) according to U.S. Pat. No. 4,224,427. Said hydrogel beads exhibit a glass transition temperature of about 99° C., an equilibrium water swelling of about 12%, and an equilibrium ethanol swelling of about 60%.

The hydrogel beads so prepared were subjected to the purification, loading, and drying steps according to Example 1 except that 50% oxprenolol HCl loading solution was prepared in methanol. The dry, loaded beads containing 37.4% of uniformly distributed drug were either controlled-extracted in water for 30 minutes or in acetone for 10 minutes before being freeze-dried as in Example 1. The in-vitro release of oxprenolol HCl from these controlled-extracted beads are compared with that of the unextracted control in FIG. 5. It is evident that, in addition to the characteristic inflection point and constant-rate release region (up to 60% of the total release), a $t_{50}$ 15 times that of the control and a time lag of about 6.5 hours are resulted from the use of acetone as the extracting solvent as compared to a $t_{50}$ 4 times that of the control and a time lag of about 0.15 hours resulted from the use of water as the extracting solvent.

EXAMPLE 6

This example illustrates the versatility of the present invention by varying the polymer morphology, mesh size, type of drug, and method of loading.

Hydrogel beads used in this example were prepared by free radical suspension polymerization of a monomer mixture identical to that of Example 5 with 50% of polypropylene glycol (MW 3,600) dissolve in the monomer mixture as diluent. After the completion of polymerization, these beads were filtered and extracted in a Soxhlet with ethanol for 3 days to remove the diluent and residual monomer before being dried and fractionated into standard mesh sizes for use in the present invention. Said hydrogel beads exhibit a glass transition temperature of about 99° C., an equilibrium water swelling of about 10%, and an equilibrium ethanol swelling of about 72%.

2.5 gm of the said hydrogel beads of $-30+35$ mesh fraction were mixed with 7.5 gm of a 35% diclofenac sodium solution in methanol and tumbled in a closed vial on a vial rotator for about 5 hours or so until all the drug solution was absorbed by the beads. The swollen, loaded beads were then dried in a laboratory fluidized bed drier at room temperature for about 15 hours to yield a drug-polymer composite system with a uniformly distributed 51.4% diclofenac sodium loading. The dry, loaded beads were controlled-extracted in water for 10 minutes before being freeze-dried as in Example 1. The in-vitro release of diclofenac sodium from these controlled-extracted beads showed a characteristic inflection point, a time-lag of about 2 minutes, and a constant-rate release region up to 60% of the total release as compared to the total absence of these characteristics in the unextracted control. In addition, the $t_{50}$'s (time to reach 50% release) of these controlled-extracted beads were increased to five times that of the unextracted control.

EXAMPLES 7-9

The process of Example 1 was repeated on hydrogel sheets containing different active agents. In all cases the in-vitro releases from systems prepared according to the present invention showed characteristic inflection points, time-lags, and extended constant-rate release regions in contrast to the total absence of these characteristics in the unextracted controls. The results are summarized in the following Table:

| Example No. | Polymer Composition | Eq. Water Swelling (%) | Tg (°C.) | Active Agent | Loading (%) | Release Results* | | | |
|---|---|---|---|---|---|---|---|---|---|
| | | | | | | Controlled-Extraction Solvent and Time | $\left(\dfrac{t_{50}}{t_{50,control}}\right)$ | Time-Lag (hr.) | Constant-Rate Release Region |
| 7 | Same as Example 1 | 25 | 116 | Oxprenolol HCl | 36.2 | Water, 30 min. Acetone, 10 min. | 1.14-1.33 | 0.15-0.30 | Up to 50% |
| 8 | 40% HEMA 20% NVP 40% MMA | 31 | 105 | 2,4-Dichlorophenoxy acetic acid, ammonium salt | 49.1 | Methanol, 20 min. | 2.0 | 0.03 | 50% |
| 9 | Polyvinyl alcohol (99% hydrolyzed, MW 116,000, and 20% crystallinity) | 80 | 70 | Oxprenolol HCl | 34.9 | Water, Acetone both 10 min. | 1.34-1.38 | 0.01-0.02 | Up to 70% |

*All in-vitro release experiments were carried out in water at 37° C.

EXAMPLE 10

This example illustrates the necessity to utilize the present invention in a glassy hydrogel system.

About 11 parts of oxprenolol HCl of particle size between about 0.5 to 5 microns were dispersed in a viscous solution containing 37 parts of ethylene vinylacetate copolymer (30% vinylacetate) and 52 parts of xylene. The rubbery ethylene vinylacetate copolymer used here has a glass transition temperature of about −25° C. with negligible water swelling. The above mentioned viscous solution was cast on a glass plate and subsequently air dried to form a film having a thickness of 0.2 mm and a 23% oxprenolol HCl loading. About 1.5 cm$^2$ of the said loaded ethylene vinylacetate film was controlled-extracted in acetone for 10 minutes before being freeze-dried as in Example 1. The in-vitro oxprenolol HCl release from this controlled-extracted sheet only showed a moderate reduction in the initial release rate as compared to the control, and similar to the control, no inflection point, time lag, or constant-rate release region was observed.

I claim:

1. An active agent containing controlled release diffusion device comprising a swellable hydrogel matrix in the non-swollen state, interpenetrated with an active agent solute having a stable concentration distribution increasing in a gradient normal to the surface of th device and between the surface and the core thereof, said gradient being in the form of a substantially continuous, inflection point containing, sigmoidal curve, wherein the core is substantially uniformly loaded with active agent and extends outwardly from the center of the device to about 1 to about 60 percent of the radius of the device; the sigmoidal concentration gradient of the active agent extending gradient of the active agent extending outwardly from said core to cover about 99 to about 30 percent of the radius of the device, the remainder, up to about 10 percent of the outermost portion of the radius to the surface of the device, contains a concentration of active agent of no more than 10 weight percent per unit volume as compared to the core concentration of active agent, such that the device, when placed in an aqueous hydrogel swelling environment, releases said active agent in a controlled continuous manner by diffusion for a predetermined period of time into said aqueous environment.

2. A device according to claim 1, wherein the device is in the form of a bead.

3. A device according to claim 2, wherein the bead has a diameter between about 0.01 mm to about 20 mm.

4. A device according to claim 1, wherein the active agent is a drug.

5. A device according to claim 3, wherein the active agent is a drug.

6. A device according to claim 1, wherein at least 40 weight percent of the active agent is released at a substantially zero-order rate.

7. A device according to claim 1, wherein at least 50 weight percent of the active agent is released at a substantially zero-order rate.

8. A device according to claim 1 wherein the hydrogel is substantially insoluble in the aqueous swelling environment of use.

9. A device according to claim 8, where the hydrogel is a crosslinked water-swellable polymer.

10. In a method of delivering an active agent solute to an aqueous environment, the improvement wherein the active agent is released from the device of claim 1.

11. A method according to claim 10, wherein the active agent is a drug.

12. A method according to claim 11, wherein the device is in the form of a bead.

* * * * *